(12) United States Patent
Larson et al.

(10) Patent No.: US 6,608,225 B1
(45) Date of Patent: Aug. 19, 2003

(54) 3-METHACRYLOXY- AND 3-ACRYLOXYISOBUTYLALKOXYSILANES

(75) Inventors: Gerald Louis Larson, Newton, PA (US); Albert-Johannes Frings, Rheinfelden (DE); Andrea Gänser, Rheinfelden (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/444,707

(22) Filed: Nov. 24, 1999

(30) Foreign Application Priority Data

Nov. 25, 1998 (DE) .......................................... 198 54 218

(51) Int. Cl.$^7$ .................................................. C07F 7/08
(52) U.S. Cl. ....................... 556/440; 524/859; 524/860; 524/866
(58) Field of Search ......................... 556/440; 524/858, 524/860, 866

(56) References Cited

U.S. PATENT DOCUMENTS

| | | | | |
|---|---|---|---|---|
| 4,946,977 A | * | 8/1990 | Bernhardt et al. | 556/440 |
| 5,103,032 A | | 4/1992 | Turner et al. | |
| 5,117,027 A | * | 5/1992 | Bernhardt et al. | 556/440 |
| 5,145,979 A | * | 9/1992 | Takatsuna et al. | 556/440 |
| 5,646,325 A | * | 7/1997 | Monkiewicz et al. | 556/440 |
| 5,789,611 A | * | 8/1998 | Isoyama et al. | 556/440 |

FOREIGN PATENT DOCUMENTS

| | | |
|---|---|---|
| DE | 1 152 695 | 8/1963 |
| DE | 1 158 071 | 11/1963 |
| DE | 44 37 666 | 4/1996 |
| DE | 44 37 667 | 4/1996 |
| EP | 0 437 653 | 7/1991 |
| EP | 0 472 438 | 2/1992 |
| EP | 0 483 480 | 5/1992 |
| EP | 0 520 477 | 12/1992 |
| EP | 0 620 206 | 10/1994 |
| EP | 0 676 403 | 10/1995 |

* cited by examiner

Primary Examiner—Paul F. Shaver
(74) Attorney, Agent, or Firm—Oblon, Spivak, McClelland, Maier & Neustadt, P.C.

(57) ABSTRACT

3-methacryloxy- and 3-acryloxyisobutylalkoxysilanes of the general formula (I)

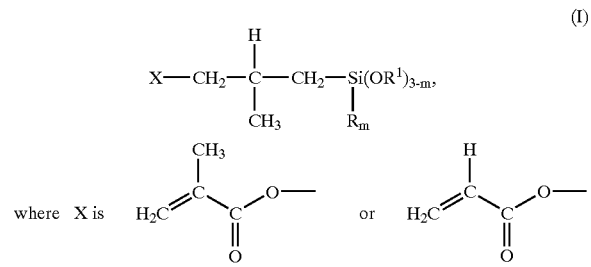

and
R is a linear alkyl radical having from 1 to 4 carbon atoms,
$R^1$ is a linear or branched alkyl radical having from 1 to 3 carbon atoms, and
m is 0 or 1.

15 Claims, No Drawings

3-METHACRYLOXY- AND 3-ACRYLOXYISOBUTYLALKOXYSILANES

BACKGROUND OF THE INVENTION

1. Field of the Invention

The present invention relates to novel 3-organo-2-methylpropylalkoxysilanes. Such compounds are also referred to as 3-organoisobutylalkoxysilanes.

The present invention also relates to processes for the preparation of 3-organo-2-methylpropylalkoxysilanes and to their use.

2. Discussion of the Background

Most organofunctional alkoxysilanes have specific technical applications. Some are used as intermediates.

For example, 3-aminopropyltrialkoxysilanes, 3-aminopropylmethyldialkoxysilanes, N-aminoethyl-3-aminopropyltrimethoxy-silane, N-aminoethyl-3-aminopropyl-methyldimethoxysilane, 3-mercaptopropyltrimethoxysilane and 3-methacryloxypropyltrimethoxysilane are used as adhesion promoters between inorganic materials and organic polymers, as crosslinking agents or as surface modification agents. Compounds such as 3-aminoisobutyltrialkoxysilanes, 3-aminoisobutylmethyldialkoxysilanes, N-(2-aminoethyl)-3-amino-2-methylpropylalkoxysilanes and N-(2-aminoethyl) 3-amino-2-methylpropylmethyldialkoxysilanes are also known (EP 0 676 403 A1, German Patent 11 58 071, DE-B 11 52 695).

It is also known that reactions of 3-chloropropyltrimethoxysilanes with potassium methacrylate in the presence of a phase transfer catalyst give 3-methacrylpropyltrimethoxyslane (EP 0 483 480 B1, EP 0 437 653 B1, DE-A 44 37 667).

There is a need for novel 3-organoisobutylalkoxysilanes.

SUMMARY OF THE INVENTION

The present invention provides 3-methacryloxy- and 3-acryloxyisobutylalkoxysilanes of the general formula (I)

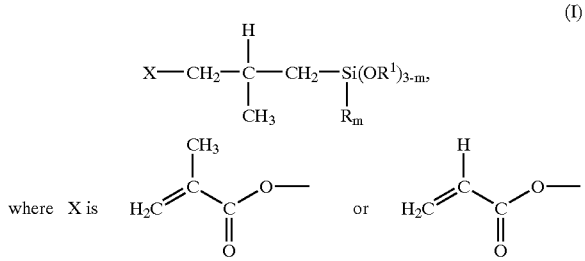

where X is and

R is a linear alkyl radical having from 1 to 4 carbon atoms,
R$^1$ is a linear or branched alkyl radical having from 1 to 3 carbon atoms, and
m is 0 or 1.

DETAILED DESCRIPTION OF THE INVENTION

The present inventors have found that reacting a 3-chloro-2-methylpropyltrialkoxysilane or a 3-chloro-2-methylpropylmethyldiethylalkoxysilane with potassium methacrylate or potassium acrylate in the presence of a phase transfer catalyst, such as is disclosed in DE-A 44 37 667, European Patent 0 483 480 and EP-A 0 437 653, gives 3-methacryloxy- or 3-acryloxyisobutylalkoxysilanes of the general formula (I) with high selectivity.

The present invention thus provides a process for the preparation of 3-methacryloxy- or 3-acryloxyisobutylalkoxysilanes of the general formula (I) by reacting alkali metal methacrylate or alkali metal acrylate, preferably potassium methacrylate or potassium acrylate, with 3-chloroisobutylalkoxysilane of the general formula (II),

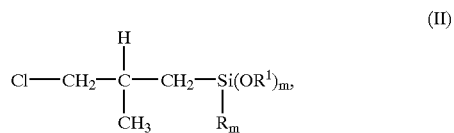

where R, R$^1$ and m are as defined above,
in the presence of at least one phase transfer catalyst and optionally in the presence of at least one stabilizer, and working up the product mixture.

In the process according to the invention, the 3-chloroisobutylalkoxysilane is preferably 3-chloroisobutyltrimethoxysilane, 3-chloroisobutyltriethoxysilane, 3-chloroisobutylmethyldimethoxysilane or 3-chloroisobutylmethyldiethoxysilane.

The present "phase transfer process" is generally carried out as already disclosed by EP 0 483 480 B1, EP 0 437 653 B1 and DE-A 44 37 667. EP 0 483 480 B1, EP 0 437 653 B1 and DE-A 44 37 667, and the contents of their respective applications, are incorporated by reference herein in their entireties.

The phase transfer catalyst can be, e.g., tetrabutylammonium bromide.

The novel compounds of the general formula (I) have a general tendency to polymerize at elevated temperature or under the influence of UV light. The addition of one or more stabilizers can stabilize the compounds according to the invention in a suitable manner both during the synthesis and also afterward. Such stabilizers are disclosed in DE-A 44 37 666, DE-A 44 37 667, U.S. Pat. No. 5,103,032, EP-A 0 620 206, EP-A 0 472 438, EP-A 0 520 477. Examples of stabilizers include: benzoquinones; hydroquinones, such as 2,5-di-t-butylhydroquinone; monoalkyl ethers of hydroquinones; amides of organic acids; isocyanurates; organofunctional and sterically hindered phenols, such as 4-(2-aminoethyl) phenol, 4-(N, N-dimethylaminomethyl)-2,6-di-t-butylphenol, 4-(N, N-dibutylaminomethyl)-2,6-di-t-butylphenol, tetrakis[methylene-3-(3',5'-di-t-butyl-4-hydroxyphenyl) propionate]methane, 2-t-butyl-6-(3'-t-butyl-5'-methyl-2-hydroxybenzyl)-4-methylphenyl acrylate, 4,4'-butylidenebis(2-t-butyl-5-methylphenol), 2,2'-butylidenebis(6-t-butyl4-methylphenol), 2,2'-ethylidene-bis(4,6-dibutylphenol), 2,2'-methylenebis(4-methyl-t-butylphenol),4,4'-methylenebis(2,6-di-t-butylphenol), n-octadecyl-3-(3',5'-di-t-butyl4'-hydroxyphenyl)propionate, 2-t-butyl-4-methoxyphenol, 2,4-di-methyl-6-t-butylphenol, 2,6-di-t-butylphenol, 2,6-di-t-butyl-4-methylphenol, 2,6-di-t-butyl-4-(α-dimethyl)aminomethylphenol, 2,6-di-butyl-4-ethylphenol, 2,6-di-t-butyl-4-methoxyphenol and (mono-, di-, tri-)α-methylbenzylphenols; alkylamines, such as propylamine, 2,2,6,6-tetramethylpiperidinooxyl and 4-hydroxy-2,2,6,6-tetramethylpiperidinooxyl; aromatic amines and N-substituted imines, such as N,N'-diphenyl-p- phenylenediamine, N,N'-dinaphthyl-p-phenylenediamine, N,N'-di(1-methylheptyl)-p-phenylenediamine, N,N'-di(1-ethyl-3-methylpentyl)-p-phenylenediamine, N,N'-di(1,4-dimethylpentyl)-p-phenylenediamine, N,N'-di-sec-butyl-p-phenylenediamine, N-phenyl-N'-cyclohexyl-p-phenylenediamine, N-phenyl-N'-isopropyl-p-phenylenediamine, 4,4'-dioctyldiphenylamine, N-methylbis (3,5-di-t-butyl4-hydroxybenzyl)amine, N,N'-diphenyl-p-quinonediimine, N,N'-di(1-methylheptyl )-p-quinonediimine, N,N'-di(1-ethyl-3-methyl-pentyl)-p-quinonediimine, N,N'-di(1,4-dimethylpentyl)-p-quinonediimine, N,N'-di-sec-butyl-p-quinonediimine, N-phenyl-N'-cyclohexyl-p-quinonediimine, and N-phenyl-N-isopropylquinonediimine; and phenothiazines, such as bis(a-methylbenzyiphenothiazine, 3,7-dioctylphenothiazine, and bis(α-dimethylbenzyl)phenothiazine.

Novel 3-methacryloxy- or 3-acryloxyisobutylalkoxysilanes of the general formula (I) already given above can be used, in particular, as adhesion promoters in filled polymers, as adhesion promoters in glass-fiber-reinforced plastics and inorganically filled organic polymers, as components for the coating of mineral wool, as components in scratch-resistant coatings, for example in the copolymerization with methyl methacrylate (MMA) in surface coatings, and as adhesion promoters in artificial stone, artificial stone slabs and artificial stone moldings, for example for sanitary articles.

The present-invention thus provides for the use of 3-methacryloxy- or 3-acryloxyisobutylalkoxysilanes of the general formula (I) already given above as adhesion promoters, as coating materials, as components in surface coatings, artificial stone and scratch-resistant coatings and also for modifying surface properties.

The present invention is illustrated in more detail by the examples below:

EXAMPLES

Example 1

3-Methacryloxyisobutyltrimethoxysilane (MAC-MEMO)

The synthesis can be carried out in a heatable stirred apparatus with compulsory stirring, gas inlet pipe, reflux condenser and dropping funnel. 547.9 g of 32% strength potassium methoxide solution (PM solution; corresponds to 2.5 mol of PM), diluted with 153.7 g of methanol and 143.4 g of methacrylic acid (MAA; corresponds to 1.7 mol of MAA) gives, at a reaction temperature of <35° C., a mixture of potassium methacrylate (PMA), methanol and methacrylic acid, the so-called 2/3 neutralized mixture. The PMA crystallizes out as fine crystals. 1213 g of N,N'-diphenyl-p-phenylenediamine(DPPD) are added to this mixture. A gas mixture consisting of 92 vol % of N and 8% of $O_2$ is then passed in below the surface. The colorless to slightly yellow reaction mixture turns deep red-orange. The DPPD is oxidized to N,N'-diphenyl-p-quinonediimine (diimine), which can be determined photometrically from the extinction at the absorption maximum of 442 nm.

For complete neutralization, a further 71.7 g=0.8 mol of MAA is added at a reaction temperature of <35° C. The pH of the reaction mixture (determined by mixing 1 part of the reaction mixture in one part deionized water) is about 10±0.5.

To this red-orange methanolic PMA suspension is added 571.2 g=2.6 mol of 3-chloro-2-methylpropyltrimethoxysilane (CMPTMO) and 21.9 g=0.03 mol of tetrabutylammonium bromide (TBAB as phase transfer catalyst). The methanol is then removed by distillation; in the end at about 30 mbar and still temperature of about 50° C.

After virtually all of the methanol has been removed (<0.1 area % GC WLD), the temperature in the still is increased to 105° C., while the mixture is stirred vigorously. After a reaction time of about 9 hours, the post-reaction is carried out at 135° C. for 2 hours. The mixture is cooled and filtered. Yield is about 226 g of moist salt and 579.8 g of red-orange mother filtrate having a diimine content of 79 g/kg (determined photometrically). 3.21 g of ionol are added to the mother filtrate. Fractional distillation under reduced pressure isolates 250.4 g=0.96 mol of MAC-MEMO with a purity of 98.5 area % GC WLD. The yield is about 39%, based on MAA or CMPTMO. At a pressure of <1 mbar the product has a boiling point of about 69° C.

Example 2

3-Acryloxyisobutyltrimethoxysilane (MAC-ACMO)

The procedure corresponds to that described above under MAC-MEMO. However, instead of 215 g of MAA, a total of 180 g=2.5 mol of acrylic acid are used.

Fractional distillation under reduced pressure isolates 272.8 g=1.17 mol of MAC-ACMO with a purity of 98.2 area % GC WLD. The yield is about 47%. based on MAA. Under a reduced pressure of <1 mbar, the product boils at about 66° C.

Obviously, numerous modifications and variations of the present invention are possible in light of the above teachings. It is therefore to be understood that within the scope of the appended claims, the invention may be practiced otherwise than as specifically described herein.

The disclosure of the priority document, patent application no. 19854218.6, which was filed in Germany on Nov. 25, 1998, is incorporated by reference herein in it entirety.

What is claimed is:

1. A compound of the general formula (I)

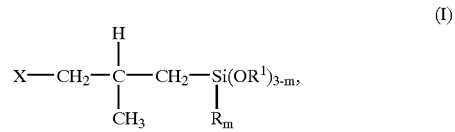

wherein X is

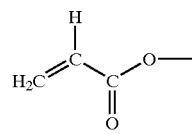

and

R is a linear alkyl group having from 1 to 4 carbon atoms, $R^1$ is a linear or branched alkyl group having from 1 to 3 carbon atoms, and m is 0 or 1.

2. The compound according to claim 1, wherein $R^1$ is a methyl group.

3. The compound according to claim 1, wherein m is 0.

4. A compound of the general formula (I)

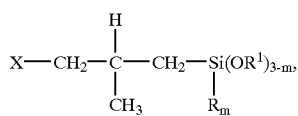

where
X is

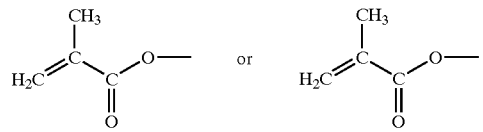

and
R is a linear alkyl group having from 1 to 4 carbon atoms,
R$^1$ is a linear or branched alkyl group having from 1 to 3 carbon atoms, and wherein m is 1.

5. The compound according to claim 1, which is 3-acryloxyisobutyl-trimethoxysilane.

6. A process for the preparation of 3-methacryloxy- or 3-acryloxyisobutylalkoxysilanes, the process comprising:

reacting an alkali metal methacrylate or an alkali metal acrylate with a 3-chloroisobutylalkoxysilane of the general formula (II)

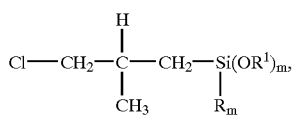

where R is a linear alkyl group having from 1 to 4 carbon atoms, R$^1$ is a linear or branched alkyl group having 1 to 3 carbon atoms, and m is 0 or 1, in the presence of at least one phase transfer catalyst; and forming a 3-methacryloxy- or 3-acryloxyisobutylalkoxysilane of the general formula (I)

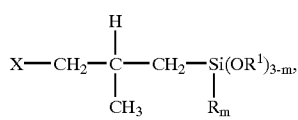

and
R, R$^1$ and m are as defined above.

7. The process according to claim 6, wherein the reacting is in the presence of at least one stabilizer.

8. The process according to claim 6, wherein the at least one phase transfer catalyst is tetrabutylammonium bromide.

9. The process according to claim 6, wherein the 3-chloroisobutylalkoxysilane of the general formula (II) is at least one of 3-chloroisobutyltrimethoxysilane, 3-chloroisobutyltriethoxysilane, 3-chloroisobutyl-methyldimethoxysilane and 3-chloroisobutylmethyldiethoxysilane.

10. The process of claim 6, wherein potassium methacrylate is reacted with a compound of general formula (II).

11. The process of claim 6, herein potassium acrylate is reacted with a compound of general formula (II).

12. The process of claim 6, wherein an alkali metal methacrylate is reacted with a compound of general formula (II).

13. The process of claim 6, wherein an alkali metal acrylate is reacted with a compound of general formula (II).

14. A filled polymer comprising a compound of the general formula (I)

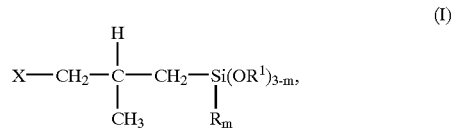

where
X is

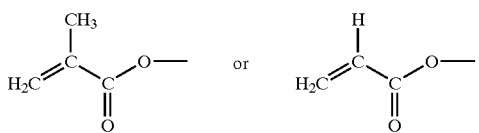

and
R is a linear alkyl group having from 1 to 4 carbon atoms,
R$^1$ is a linear or branched alkyl group having from 1 to 3 carbon atoms, and
m is 0 or 1.

15. A glass-fiber-reinforced plastic composition comprising a compound of the general formula (I)

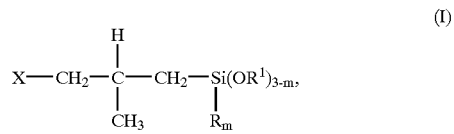

where
X is

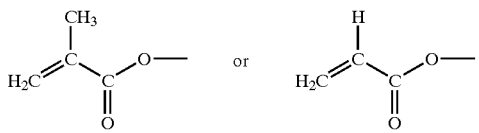

and
R is a linear alkyl group having from 1 to 4 carbon atoms,
R$^1$ is a linear or branched alkyl group having from 1 to 3 carbon atoms, and m is 0 or 1.

* * * * *